(12) United States Patent
Amerling et al.

(10) Patent No.: US 12,405,328 B2
(45) Date of Patent: Sep. 2, 2025

(54) FULL BODY POSTERIOR COIL FOR A MAGNETIC RESONANCE IMAGING SYSTEM

(71) Applicant: GE Precision Healthcare LLC, Wauwatosa, WI (US)

(72) Inventors: Robert John Amerling, Milwaukee, WI (US); Jiaqi Li, Pewaukee, WI (US); Mark Giancola, Chesterland, OH (US); Jason Lee Philps, Merton, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 158 days.

(21) Appl. No.: 18/094,600

(22) Filed: Jan. 9, 2023

(65) Prior Publication Data

US 2024/0230801 A1 Jul. 11, 2024

(51) Int. Cl.
*G01R 33/34* (2006.01)
*A61B 5/00* (2006.01)
*A61B 5/055* (2006.01)

(52) U.S. Cl.
CPC ........ *G01R 33/34084* (2013.01); *A61B 5/055* (2013.01); *A61B 5/704* (2013.01)

(58) Field of Classification Search
None
See application file for complete search history.

(56) References Cited

U.S. PATENT DOCUMENTS

| | | | |
|---|---|---|---|
| 6,980,002 B1 | 12/2005 | Petropoulos et al. | |
| 7,049,819 B2 | 5/2006 | Chan et al. | |
| 8,046,046 B2 | 10/2011 | Chan et al. | |
| 8,179,136 B2 | 5/2012 | Chan et al. | |
| 8,369,929 B2 | 2/2013 | Scarth et al. | |
| 8,603,014 B2 | 12/2013 | Alleman et al. | |
| 8,613,714 B2 | 12/2013 | Alleman et al. | |
| 8,840,542 B2 | 9/2014 | Plata | |
| 9,494,664 B2 | 11/2016 | Taracila et al. | |
| 2011/0267059 A1* | 11/2011 | Shvartsberg | G01R 33/34084 324/318 |
| 2013/0218000 A1 | 8/2013 | Coppens et al. | |
| 2013/0320981 A1 | 12/2013 | Bulumulla et al. | |
| 2013/0320982 A1 | 12/2013 | Bulumulla et al. | |
| 2014/0323851 A1 | 10/2014 | Barberi et al. | |
| 2018/0263561 A1* | 9/2018 | Jones | G01R 33/34007 |

(Continued)

FOREIGN PATENT DOCUMENTS

JP 2011521749 7/2011

*Primary Examiner* — Keith M Raymond
*Assistant Examiner* — Ashish S Jasani
(74) *Attorney, Agent, or Firm* — Fletcher Yoder, P.C.

(57) ABSTRACT

A magnetic resonance imaging (MRI) system includes an MRI scanner having a bore. The MRI system also includes a table including a cradle and a posterior radio frequency (RF) receiving coil array assembly integrated on a top surface of the cradle, wherein the table is configured to move a subject to be imaged disposed on the RF receiving coil array assembly into and out of the bore of the MRI scanner, and wherein the posterior RF receiving coil array assembly comprises a plurality of sections, each section of the plurality of sections includes an RF coil including a plurality of loops, and at least one section of the plurality of sections is configured to be manipulated into a bent position and to remain in the bent position without extraneous support.

8 Claims, 8 Drawing Sheets

(56) References Cited

U.S. PATENT DOCUMENTS

| | | | | |
|---|---|---|---|---|
| 2019/0154773 A1* | 5/2019 | Stack | ............... | G01R 33/34084 |
| 2019/0154775 A1* | 5/2019 | Stack | ................ | G01R 33/3685 |
| 2019/0310328 A1* | 10/2019 | Fuqua | ................ | G01R 33/3657 |
| 2021/0132164 A1 | 5/2021 | Fuqua et al. | | |

* cited by examiner

FULL BODY POSTERIOR COIL FOR A MAGNETIC RESONANCE IMAGING SYSTEM

BACKGROUND

The subject matter disclosed herein relates to medical imaging and, more particularly, to a full body coil for a magnetic resonance imaging (MRI) system.

Non-invasive imaging technologies allow images of the internal structures or features of a patient/object to be obtained without performing an invasive procedure on the patient/object. In particular, such non-invasive imaging technologies rely on various physical principles (such as the differential transmission of X-rays through a target volume, the reflection of acoustic waves within the volume, the paramagnetic properties of different tissues and materials within the volume, the breakdown of targeted radionuclides within the body, and so forth) to acquire data and to construct images or otherwise represent the observed internal features of the patient/object.

During MRI, when a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment, $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradient fields vary according to the particular localization method being used. The resulting set of received nuclear magnetic resonance (NMR) signals are digitized and processed to reconstruct the image using one of many well-known reconstruction techniques.

In MRI, the workflow around removing and/or installing surface coils (e.g., for imaging particular areas of a patient such as a head, foot, leg, etc.) and the numerous patient positioning pads between patients can be cumbersome and time consuming depending on the type of scan and patient body types. The current rigid surface coils also do not perfectly fit all patients, thus, requiring shimming pads to get as close as possible. The closer the coil loops are to the selected anatomy, the better.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a magnetic resonance imaging (MRI) system is provided. The MRI system includes an MRI scanner having a bore. The MRI system also includes a table including a cradle and a posterior radio frequency (RF) receiving coil array assembly integrated on a top surface of the cradle, wherein the table is configured to move a subject to be imaged disposed on the RF receiving coil array assembly into and out of the bore of the MRI scanner, and wherein the posterior RF receiving coil array assembly includes a plurality of sections, each section of the plurality of sections includes an RF coil including a plurality of loops, and at least one section of the plurality of sections is configured to be manipulated into a bent position and to remain in the bent position without extraneous support.

In another embodiment, a posterior radio frequency (RF) receiving coil array assembly for a magnetic resonance imaging (MRI) system is provided. The posterior RF receiving coil array assembly includes a plurality of sections, wherein each section of the plurality of sections includes an RF coil including a plurality of loops, and at least one section of the plurality of sections is configured to be manipulated into a bent position and to remain in the bent position without extraneous support, wherein the posterior RF receiving coil array assembly is configured to be integrated on a top surface of a cradle of a table configured to move a subject to be imaged disposed on the RF receiving coil array assembly into and out of a bore of an MRI scanner of the MRI system.

In a further embodiment, a posterior RF receiving coil array assembly for a magnetic resonance imaging (MRI) system is provided. The posterior RF receiving coil array assembly a plurality of padded sections, each padded section of the plurality of padded sections includes an RF coil including a plurality of loops, and multiple padded sections of the plurality of padded sections include a mechanically resistive structure configured both to be manipulated so that a respective padded section is in a bent position and to keep the respective padded section in the bent position without extraneous support, wherein the posterior RF receiving coil array assembly is configured to be integrated on a top surface of a cradle of a table configured to move a subject to be imaged disposed on the RF receiving coil array assembly into and out of a bore of an MRI scanner of the MRI system.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
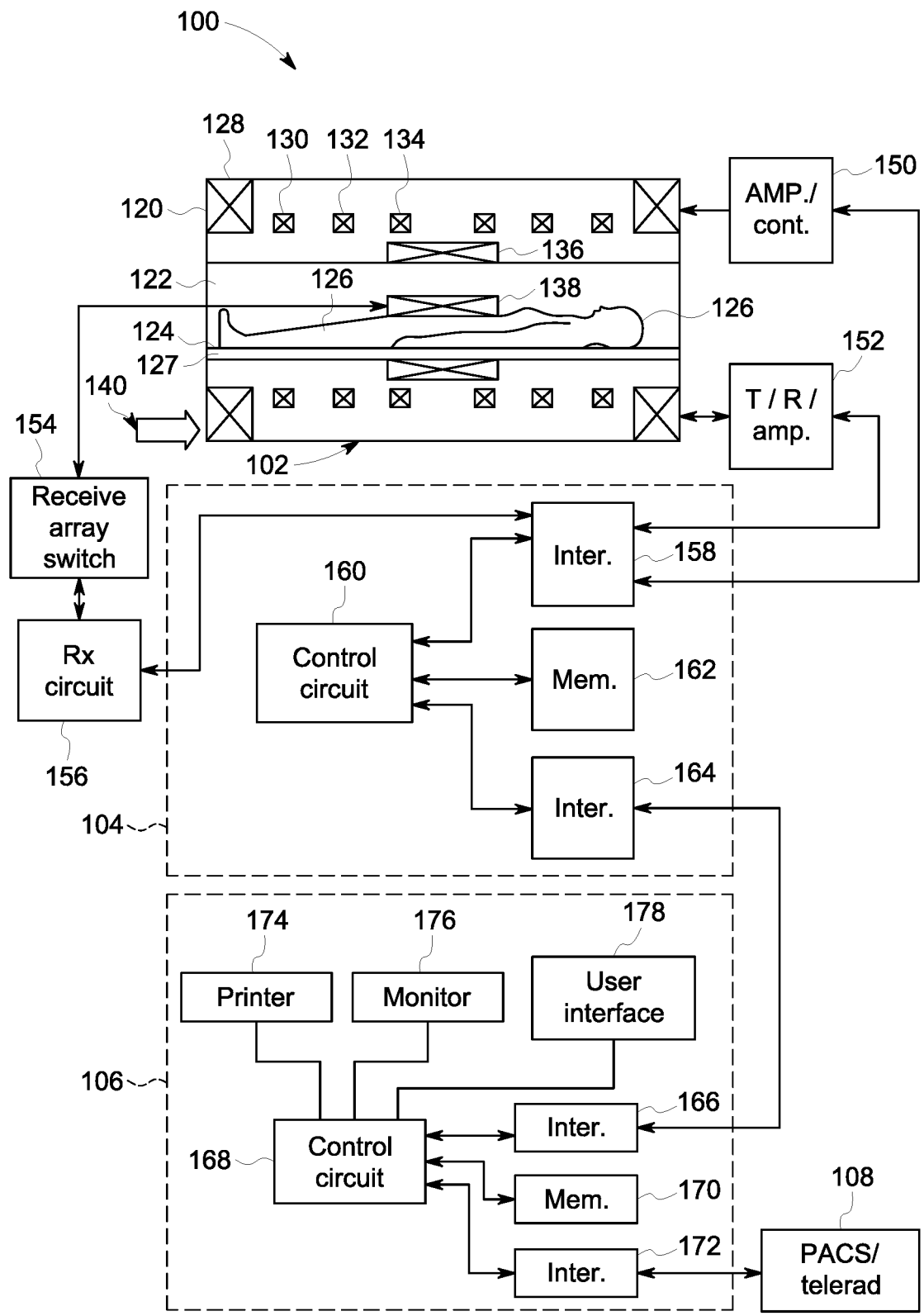
FIG. 1 illustrates an embodiment of a magnetic resonance imaging (MRI) system suitable for use with the disclosed technique.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion are provided in the context of medical imaging, it should be appreciated that the disclosed techniques are not limited to such medical contexts. Indeed, the provision of examples and explanations in such a medical context is only to facilitate explanation by providing instances of real-world implementations and applications. However, the disclosed techniques may also be utilized in other contexts, such as image reconstruction for non-destructive inspection of manufactured parts or goods (i.e., quality control or quality review applications), and/or the non-invasive inspection of packages, boxes, luggage, and so forth (i.e., security or screening applications). In general, the disclosed techniques may be useful in any imaging or screening context or image processing or photography field where a set or type of acquired data undergoes a reconstruction process to generate an image or volume.

The present disclosure provides for a full body coil for an MRI system. In particular, a posterior radio frequency (RF) receiving coil array assembly is provided that is integrated on a top surface of a cradle of a table that moves a patient (e.g., subject) into and out of a bore an MRI scanner of the MRI system. The posterior RF receiving coil array assembly is formed by multiple sections (e.g. padded sections). Each section includes an RF coil having multiple loops (e.g., elements or channels). One or more sections are configured to be manipulated into a bent position and to remain in the bent position without extraneous support. In particular, the one or more sections are configured to be bent about the patient's anatomy from a posterior surface toward an anterior surface (and in some cases disposed about a portion of the anterior surface). Each of the sections is configured to be bent or manipulated include a mechanically resistive structure (e.g., disposed within a padded enclosure) to keep the sections in the bent position without extraneous support (e.g., from shims). The posterior RF receiving coil array assembly extends across an entirety of the top surface of the cradle. In certain embodiments, the posterior RF receiving coil array assembly can be utilized on both a posterior surface and an anterior surface of a pediatric patient without utilizing any additional RF receiving coil array assembly during an imaging scan of the pediatric patient by the MRI system.

The disclosed embodiments enable the posterior RF receiving coil array to be disposed closer to the anatomy of the patient being imaged. The disclosed embodiments enable for better in-table patient positioning and remove the need for comfort tilt accessories. In addition, the disclosed embodiments alleviate issues of carrying around large and somewhat clumsy surface coils for quicker workflow. The disclosed embodiments further provide better contour fitting and comfort to different patient types which boosts image quality. The disclosed embodiments reduce trips to coils closet and overall setup time for the patients while also providing a closer loop-to-anatomy distance to optimize image quality. Even further, by improving workflow with less trips and providing more integrated capability all at the table, the throughput of scanning patients is increased.

With the preceding in mind, FIG. 1 a magnetic resonance imaging (MRI) system 100 is illustrated schematically as including a scanner 102, scanner control circuitry 104, and system control circuitry 106. According to the embodiments described herein, the MRI system 100 is generally configured to perform MR imaging.

System 100 additionally includes remote access and storage systems or devices such as picture archiving and communication systems (PACS) 108, or other devices such as teleradiology equipment so that data acquired by the system 100 may be accessed on- or off-site. In this way, MR data may be acquired, followed by on- or off-site processing and evaluation. While the MRI system 100 may include any suitable scanner or detector, in the illustrated embodiment, the system 100 includes a full body scanner 102 having a housing 120 through which a bore 122 is formed. A table 124 is moveable into the bore 122 to permit a patient 126 (e.g., subject) to be positioned therein for imaging selected anatomy within the patient 126. The portion of the table 124 that the patient is 126 disposed on and that is moved into and out of the bore 122 is a cradle 127.

Scanner 102 includes a series of associated coils for producing controlled magnetic fields for exciting the gyromagnetic material within the anatomy of the patient being imaged. Specifically, a primary magnet coil 128 is provided for generating a primary magnetic field, $B_0$, which is generally aligned with the bore 122. A series of gradient coils 130, 132, and 134 permit controlled magnetic gradient fields to be generated for positional encoding of certain gyromagnetic nuclei within the patient 126 during examination sequences. A radio frequency (RF) coil 136 (e.g., RF transmit coil) is configured to generate radio frequency pulses for exciting the certain gyromagnetic nuclei within the patient. In addition to the coils that may be local to the scanner 102, the system 100 also includes a set of receiving coils or RF receiving coils 138 (e.g., an array of coils) configured for placement proximal (e.g., against) to the patient 126. As an example, the receiving coils 138 can include cervical/thoracic/lumbar (CTL) coils, head coils, single-sided spine coils, and so forth. Generally, the receiving coils 138 are placed close to or on top of the patient 126 so as to receive the weak RF signals (weak relative to the transmitted pulses generated by the scanner coils) that are generated by certain gyromagnetic nuclei within the patient 126 as they return to their relaxed state.

The various coils of system 100 are controlled by external circuitry to generate the desired field and pulses, and to read emissions from the gyromagnetic material in a controlled manner. In the illustrated embodiment, a main power supply 140 provides power to the primary field coil 128 to generate the primary magnetic field, $B_0$. A power input (e.g., power from a utility or grid), a power distribution unit (PDU), a power supply (PS), and a driver circuit 150 may together provide power to pulse the gradient field coils 130, 132, and 134. The driver circuit 150 may include amplification and control circuitry for supplying current to the coils as defined by digitized pulse sequences output by the scanner control circuitry 104.

Another control circuit 152 is provided for regulating operation of the RF coil 136. Circuit 152 includes a switching device for alternating between the active and inactive modes of operation, wherein the RF coil 136 transmits and does not transmit signals, respectively. Circuit 152 also includes amplification circuitry configured to generate the RF pulses. Similarly, the receiving coils 138 are connected to switch 154, which is capable of switching the receiving coils 138 between receiving and non-receiving modes. Thus, the receiving coils 138 resonate with the RF signals produced by relaxing gyromagnetic nuclei from within the patient 126 while in the receiving mode, and they do not resonate with RF energy from the transmitting coils (i.e., coil 136) so as to prevent undesirable operation while in the non-receiving mode. Additionally, a receiving circuit 156 is configured to receive the data detected by the receiving coils 138 and may include one or more multiplexing and/or amplification circuits.

It should be noted that while the scanner 102 and the control/amplification circuitry described above are illustrated as being coupled by a single line, many such lines may be present in an actual instantiation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner and either or both of the scanner and system control circuitry 104, 106.

As illustrated, scanner control circuitry 104 includes an interface circuit 158, which outputs signals for driving the gradient field coils and the RF coil and for receiving the data representative of the magnetic resonance signals produced in examination sequences. The interface circuit 158 is coupled to a control and analysis circuit 160. The control and analysis circuit 160 executes the commands for driving the circuit 150 and circuit 152 based on defined protocols selected via system control circuit 106.

Control and analysis circuit 160 also serves to receive the magnetic resonance signals and performs subsequent processing before transmitting the data to system control circuit 106. Scanner control circuit 104 also includes one or more memory circuits 162, which store configuration parameters, pulse sequence descriptions, examination results, and so forth, during operation.

Interface circuit 164 is coupled to the control and analysis circuit 160 for exchanging data between scanner control circuitry 104 and system control circuitry 106. In certain embodiments, the control and analysis circuit 160, while illustrated as a single unit, may include one or more hardware devices. The system control circuit 106 includes an interface circuit 166, which receives data from the scanner control circuitry 104 and transmits data and commands back to the scanner control circuitry 104. The control and analysis circuit 168 may include a CPU in a multi-purpose or application specific computer or workstation. Control and analysis circuit 168 is coupled to a memory circuit 170 to store programming code for operation of the MRI system 100 and to store the processed image data for later reconstruction, display and transmission. The programming code may execute one or more algorithms that, when executed by a processor, are configured to perform reconstruction of acquired data as described below. In certain embodiments, image reconstruction may occur on a separate computing device having processing circuitry and memory circuitry.

An additional interface circuit 172 may be provided for exchanging image data, configuration parameters, and so forth with external system components such as remote access and storage devices 108. Finally, the system control and analysis circuit 168 may be communicatively coupled to various peripheral devices for facilitating operator interface and for producing hard copies of the reconstructed images. In the illustrated embodiment, these peripherals include a printer 174, a monitor 176, and user interface 178 including devices such as a keyboard, a mouse, a touchscreen (e.g., integrated with the monitor 176), and so forth.

Figure 2:
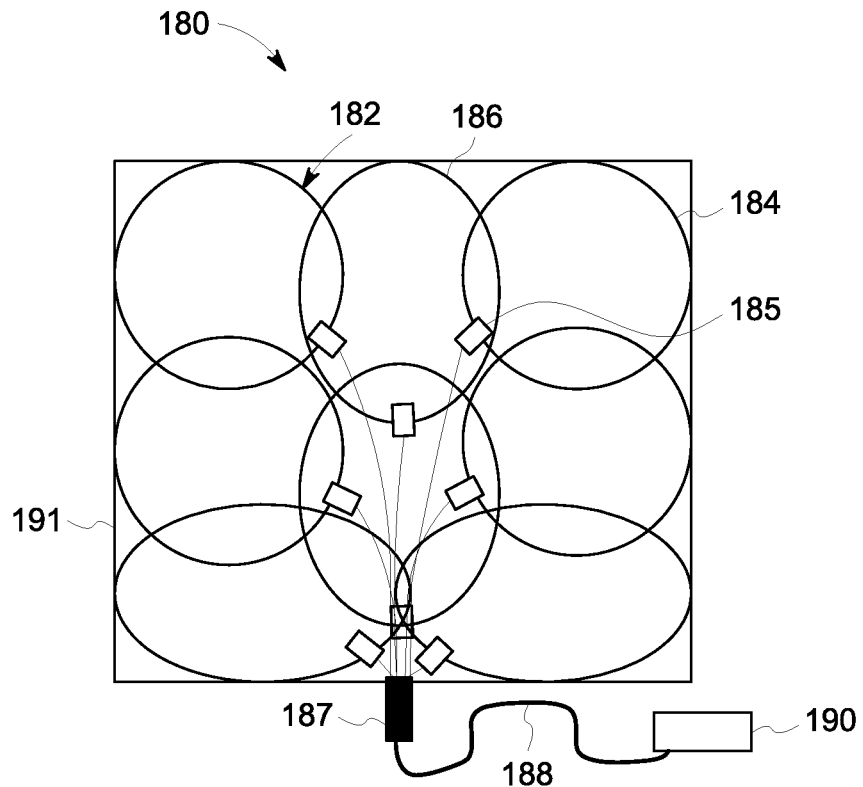
FIG. 2 is a schematic diagram of an RF coil array section and is topology, in accordance with aspects of the present disclosure.

FIG. 2 is a schematic diagram of an RF coil array section 180 (e.g., RF receiving coil array section) and its topology. As described in greater detail below, the RF coil array section 180 is one section 180 of a plurality of sections 180 forming a posterior RF receiving coil array assembly integrated on a top surface of a cradle. The shape and dimensions of each section may vary from that depicted in FIG. 2. The RF coil array section 180 may be utilized in an MRI system (e.g., MRI system 100 in FIG. 1). The RF coil array section 180 includes an RF coil 182 (e.g., flexible RF coil) having a plurality of loops 184 (e.g., elements or channels) with each loop 184.

As depicted in FIG. 2, the plurality of loops 184 includes 8 loops (although the number of loops 184 may vary). Each loop 184 is coupled to an electronics unit 185 coupled to a coil-interfacing cable 186. The coil-interfacing cables 186 of each of the loops 184 is coupled to a balun 187 (e.g., integrated balun cable harness). Each electronics unit 185 may include various components (e.g., a decoupling circuit, an impedance inverter circuit, and a pre-amplifier). The balun 187 may act as an RF trap. The balun 187 is coupled (via a cable 188) to a P connector 190 (e.g., port connector) that enables the RF coil array 180 to be coupled to the interface of the MRI system that couples imaging components to processing components. In certain embodiments, the coil-interfacing cables 186 for the loops 184 of RF coils 182 of multiple sections forming the posterior RF receiving coil array assembly may be coupled to a common balun 187 coupled to the P connector 190 or coupled to separate baluns 187 coupled to a common P connector 190.

The loops 184 are disposed within an enclosure 191. In certain embodiments, the enclosure may be flexible. As depicted in FIG. 2, each loop 184 partially overlaps with at least one adjacent loop 184. In certain embodiments, one or more of the RF coils 182 may be designed utilizing AIR™ coil technology from General Electric Healthcare. This enables the RF coil 182 to be lightweight and flexible.

Figure 3:
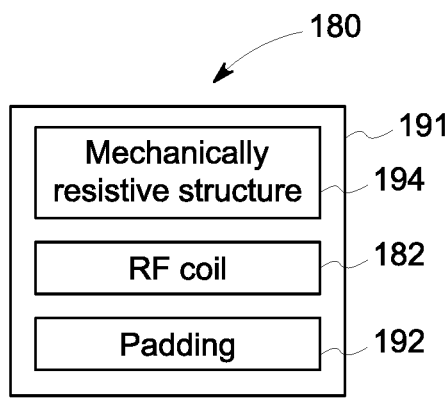
FIG. 3 is a schematic diagram of an RF coil array section and its components, in accordance with aspects of the present disclosure.
Figure 4:
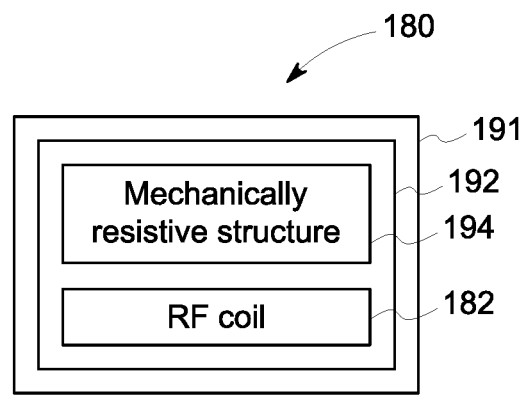
FIG. 4 is a schematic diagram of an RF coil array section and its components (e.g., having padding incorporated in an enclosure), in accordance with aspects of the present disclosure.
Figure 7:
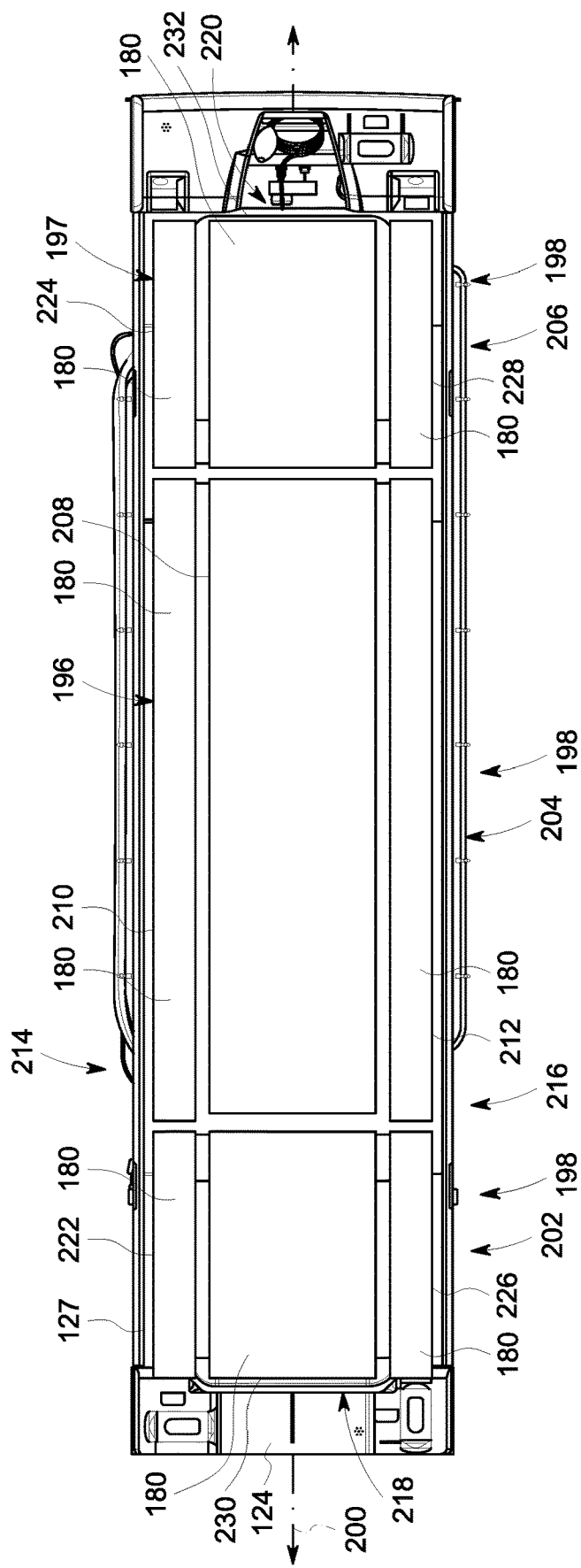
FIG. 7 is a schematic diagram of a posterior RF receiving coil array assembly disposed on a cradle of a table of the MRI system in FIG. 1, in accordance with aspects of the present disclosure.

FIGS. 3 and 4 are schematic diagrams of the RF coil array section 180 and its components for some of the sections forming a posterior RF receiving coil array assembly (e.g., posterior RF receiving coil array assembly 196 in FIG. 7). Each RF coil array section 180 includes the enclosure 191. The RF coil 182 is disposed within the enclosure 191. The RF coil array section 180 is a padded section (e.g., pillow-type structure). In certain embodiments, the RF coil array section 180 includes padding 192 disposed within the enclosure 191 as depicted in FIG. 3. In certain embodiments, the padding 192 is integrated as part of the enclosure 191 as depicted in FIG. 4. The RF coil array section 180 further includes a mechanically resistive structure 194 disposed within the enclosure 191. The mechanically resistive structure 194 is configured to be manipulated (e.g., bent) to a particular position (e.g., bent position) and maintain the position without extraneous support (e.g., from a shim). Thus, the RF coil array section 180 is also configured to be manipulated (e.g., bent) to a particular position (e.g., bent position) and maintain the position without extraneous support. By manipulating the position of the RF coil array section 180, the shape of the RF coil array section 180 is also changed. The mechanically resistive structure 194 is made of a material that is compatible with MRI. The RF coil 182 and its loops are flexible to accommodate the changing of the position (and shape) of the RF coil array section.

Figure 5:
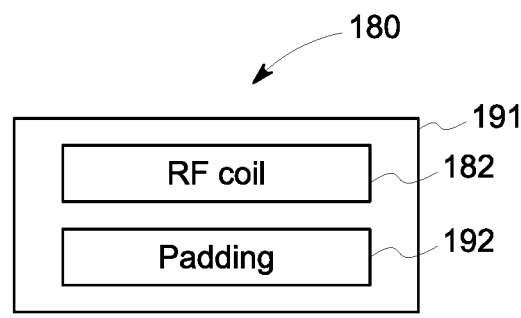
FIG. 5 is a schematic diagram of an RF coil array section and its components (e.g., lacking a mechanically resistive structure), in accordance with aspects of the present disclosure.
Figure 6:
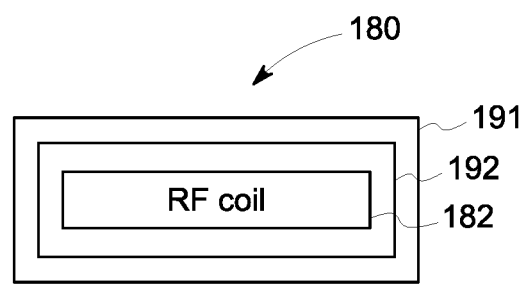
FIG. 6 is a schematic diagram of an RF coil array and its components (e.g., lacking a mechanically resistive structure and having padding incorporated in an enclosure), in accordance with aspects of the present disclosure.

FIGS. 5 and 6 are schematic diagrams of the RF coil array section 180 and its components for some of the sections forming a posterior RF receiving coil array assembly (e.g., posterior RF receiving coil array assembly 196 in FIG. 7). Each RF coil array section 180 includes the enclosure 191. The RF coil 182 is disposed within the enclosure 191. The RF coil array section 180 is a padded section (e.g., pillow-type structure). In certain embodiments, the RF coil array section 180 includes padding 192 disposed within the enclosure 191 as depicted in FIG. 3. In certain embodiments, the padding 192 is integrated as part of the enclosure 191 as depicted in FIG. 4. The RF coil array section 180 lacks a mechanically resistive structure and is not configured to be manipulated (e.g., bent) to a particular position (e.g., bent position). In certain embodiments, the RF coil 182 and its loops of the RF coil array sections 180 in FIGS. 5 and 6 may be rigid.

FIG. 7 is a schematic diagram of a posterior RF receiving coil array assembly 196 disposed on the cradle 127 of the table 124 of the MRI system 100 in FIG. 1. As depicted, the posterior RF receiving coil array assembly 196 is disposed across an entirety of a top surface 197 of the cradle 127. The posterior RF receiving coil array assembly 196 is coupled to (e.g., integrated with) the top surface 197 of the cradle 127.

The posterior RF receiving coil array assembly 196 is formed from multiple RF coil array sections 180. As noted above, these sections 180 are padded and each section 180 includes the RF coil having loops. As depicted in FIG. 7, the posterior RF receiving coil array assembly 196 includes 9 RF coil array sections 180. The number of RF coil array sections 180 in the posterior RF receiving coil array assembly 196 may vary.

As depicted in FIG. 7, the RF coil array sections 180 located in different regions 198 (e.g., axial locations) along a longitudinal axis 200 of the posterior RF receiving coil array assembly 196 (and the cradle 127). For example, a first plurality of RF coil array sections 180 are located at a first region 202 (e.g., first axial location), a second plurality of RF coil array sections 180 are located at a second region 204 (e.g., second axial location), and a third plurality of RF coil array sections 180 are located at a third region 206 (e.g., third axial location) along the longitudinal axis 200. The number of regions 198 of multiple RF coil sections 180 at different axial locations along the longitudinal axis 200 may vary. As depicted, each region 198 includes 3 RF coil array sections 180. In certain embodiments, each region 198 has the same number of RF coil array sections 180. In certain embodiments, at least two of the regions 198 may have a different number of RF coil array sections 180. As depicted, at least two of the RF coil array sections 180 in each region 190 differ in dimensions. In certain embodiments, all of the RF coil array sections 180 in each region 190 may differ in dimensions. In certain embodiments, all of the RF coil array sections 180 in each region 198 may have the same dimensions. In certain embodiments, corresponding RF coil array sections 180 in each of the regions 198 may have different dimensions. In certain embodiments, corresponding RF coil array sections 180 in each of the regions 198 may have similar dimensions.

Each region 198 is configured to be disposed on the top surface 197 of the cradle 127 below a posterior surface of a patient to be imaged. In each region 198, at least one RF coil array section 180 is configured to be manipulated (e.g., bent) into a particular position (e.g., bent position) due to having a mechanically resistive structure (e.g., mechanically resistive structure 194 in FIGS. 3 and 4). In particular, the at least one RF coil array section 180 is configured to be bent about the patient's anatomy from a posterior surface toward an anterior surface (and in some cases disposed about a portion of the anterior surface). In certain regions 198, at least two RF coil array section 180 are configured to be manipulated (e.g., bent) into a particular position (e.g., bent position) due to having a mechanically resistive structure. In certain regions 198, all of the RF coil array sections 180 are configured to be manipulated (e.g., bent) into a particular position (e.g., bent position) due to having a mechanically resistive structure.

In certain regions, at least one RF coil array section 180 is configured to not be bent (i.e., lacks a mechanically resistive structure). As describe above, this type of section may include a rigid RF coil. In certain embodiments, the at least one RF coil array section 180 that is not configured to be bent is centrally located (e.g., RF coil array section 208 in FIG. 7). In certain embodiments, the RF coil array section 180 (e.g., RF coil array section 208) is flanked by RF coil array sections 180 that are configured to be bent (e.g., RF coil array sections 210, 212 in the second region 204.

The cradle 127 includes lateral edges 214, 216 and longitudinal edges or ends 218, 220 relative to the longitudinal axis 200. In certain embodiments, each of the RF coil array sections 180 (e.g., RF coil array sections 210, 212, 222, 224, 226, 228) adjacent the lateral edges 214, 216 are configured to be manipulated (e.g., bent) into a particular position (e.g., bent position) due to having a mechanically resistive structure. In certain embodiments, some of the RF coil array sections 180 adjacent the longitudinal edges 218, 220 are configured to be manipulated (e.g., bent) into a particular position (e.g., bent position) due to having a mechanically resistive structure. In certain embodiments, the centrally located RF coil array sections 180 adjacent the longitudinal edges 218, 220 (e.g., RF coil array sections 230, 232) are not configured to be manipulated into a bent position (e.g., due to lack of a mechanically resistive structure). In certain embodiments, each RF coil array section 180 adjacent the longitudinal edges 218, 220 (e.g., RF coil array sections 222, 224, 226, 228, 230, 232) are configured to be manipulated (e.g., bent) into a particular position (e.g., bent position) due to having a mechanically resistive structure.

As mentioned above, the posterior RF receiving coil array assembly 196 is integrated on the top surface 197 on the cradle 127 of the table 124. The posterior RF receiving coil array assembly 196 is integrated to the top surface 197 by coupling one or more of the RF coil array sections 180 to the top surface 197. The one or more RF coil array sections 180 that are not configured to be bent (e.g., due to lacking a mechanically resistive structure) are the RF coil array sections 180 directly coupled to the top surface 197 via one or more fasteners (straps, hook and loop fasteners, rivets, etc.). For example, centrally located RF coil array section 208 (which is not configured to be manipulated into a bent position) may be directly coupled to top surface 197. The one or more RF coil array sections 180 that are configured to be manipulated into a bent position are not directly coupled to the top surface 197 of the cradle 127 but are instead indirectly coupled to the top surface 197 (e.g., via the one or more RF coil array sections 180 that are not configured to be bent that are directly coupled to the top surface 197 of the cradle 127).

Figure 8:
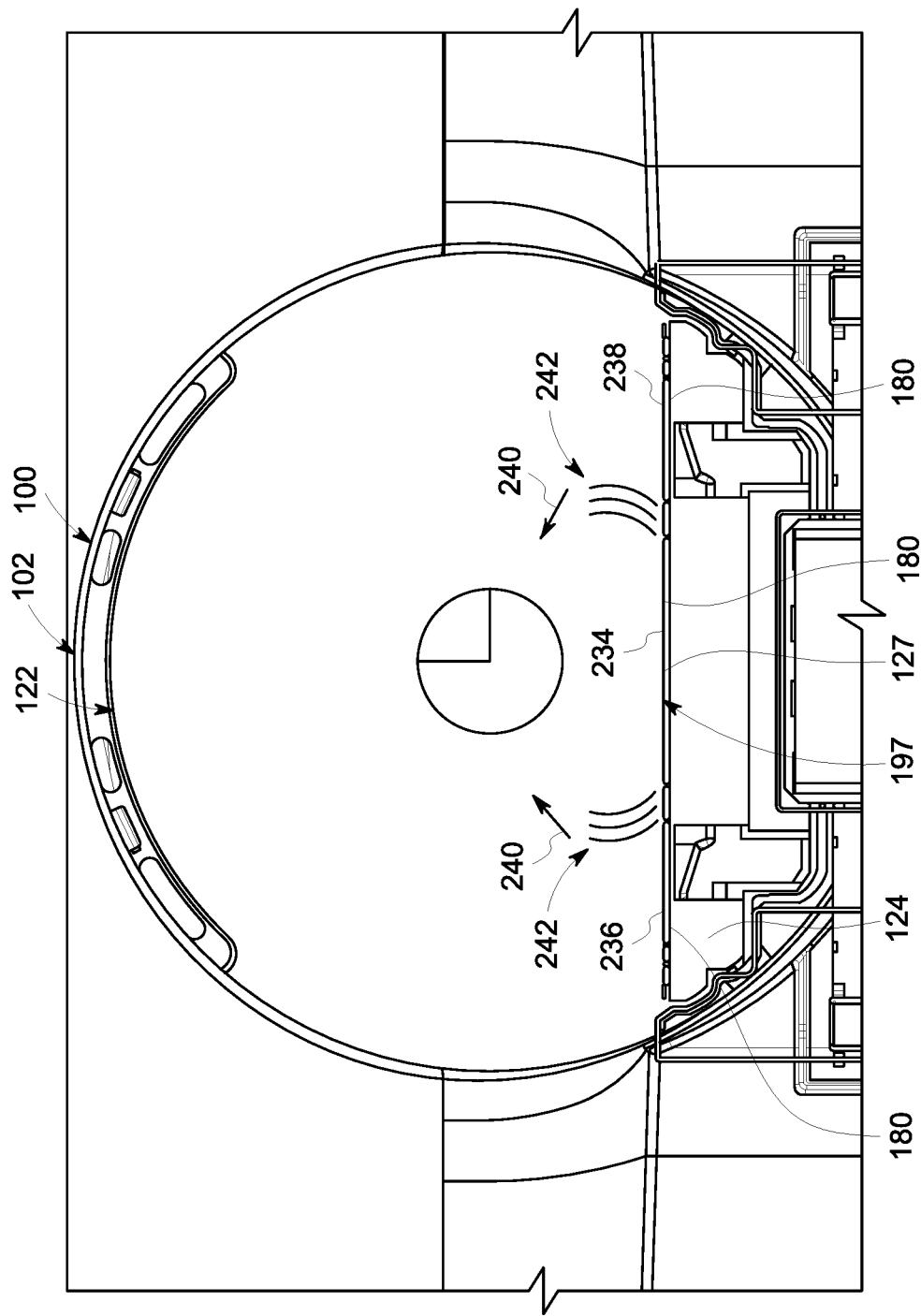
FIG. 8 is a schematic diagram of an end view of a posterior RF receiving coil array assembly disposed within a bore of an MRI system, in accordance with aspects of the present disclosure.

FIG. 8 is a schematic diagram of an end view of the posterior RF receiving coil array assembly 196 disposed within a bore 122 of the MRI scanner 102 of the MRI system 100. As depicted in FIG. 8, the posterior RF receiving coil array assembly 196 is integrated on the top surface 197 of the cradle 127 of the table 124. As depicted, the posterior RF receiving coil array assembly includes multiple RF coil array sections 180. In particular, the posterior RF receiving coil array assembly 196 includes a central RF coil array section 234 flanked by a pair of RF coil array sections 236, 238. Each RF coil array section 234, 236, 238 is a padded section. Each RF coil array section 234, 236, 238 is configured to be disposed beneath a posterior surface of a patient to be imaged. The central RF coil array section 234 is not configured to be manipulated or bent (i.e., the central RF coil array section 234 lacks a mechanically resistive structure). In certain embodiments, the central RF coil array section 234 includes a rigid RF coil. The RF coil array sections 236, 238 each include a mechanically resistive structure that enables each RF coil array section 236, 238 to be manipulated (e.g., bent) into a variety of positions (e.g., bent positions) and maintain these positions without extraneous support (e.g., without support from shims). Each RF coil array section 236, 238 may have a flexible RF coil. As depicted in FIG. 8, each RF coil array sections 236, 238 can be manipulated in partially radial and partially circumferential direction as indicated by the arrows 240 into a plurality of different positions 242 (e.g., bent or curved positions) and maintain these positions 242 without extraneous support. The RF coil array sections 236, 238 are configured to be bent about the patient's anatomy from a posterior surface toward an anterior surface (and in some cases disposed about a portion of the anterior surface).

Figure 9:
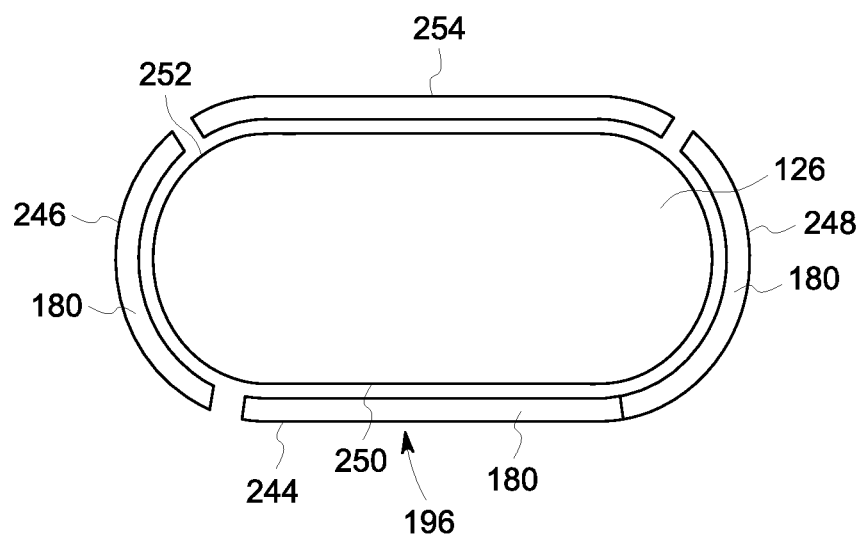
FIG. 9 is a schematic diagram of RF array coil sections of a posterior RF receiving coil array assembly disposed about a portion of a patient, in accordance with aspects of the present disclosure.

FIG. 9 is a schematic diagram of RF array coil sections 180 of the posterior RF receiving coil array assembly 196 disposed about a portion of the patient 126. In FIG. 9, the patient 126 may be an adult patient. As depicted, the posterior RF receiving coil array assembly 196 includes multiple RF coil array sections 180. In particular, the posterior RF receiving coil array assembly 196 includes a central RF coil array section 244 flanked by a pair of RF coil array sections 246, 248. Each RF coil array section 244, 246, 248 is a padded section. Each RF coil array section 244, 246, 248 is configured to be disposed beneath a posterior surface 250 of the patient 126 to be imaged. The central RF coil array section 244 is not configured to be manipulated or bent (i.e., the central RF coil array section 244 lacks a mechanically resistive structure). In certain embodiments, the central RF coil array section 244 includes a rigid RF coil. The RF coil array sections 246, 248 each include a mechanically resistive structure that enables each RF coil array section 246, 248 to be manipulated (e.g., bent) into a variety of positions (e.g., bent positions) and maintain these positions without extraneous support (e.g., without support from shims). Each RF coil array section 246, 248 may have a flexible RF coil. As depicted in FIG. 9, each RF coil array sections 246, 248 bent about the patient 126 from the posterior surface 250 toward an anterior surface 252. As depicted in FIG. 9, a separate surface coil array 254 (e.g., anterior RF receiving coil array) is during the MRI imaging of the patient 126.

Figure 10:
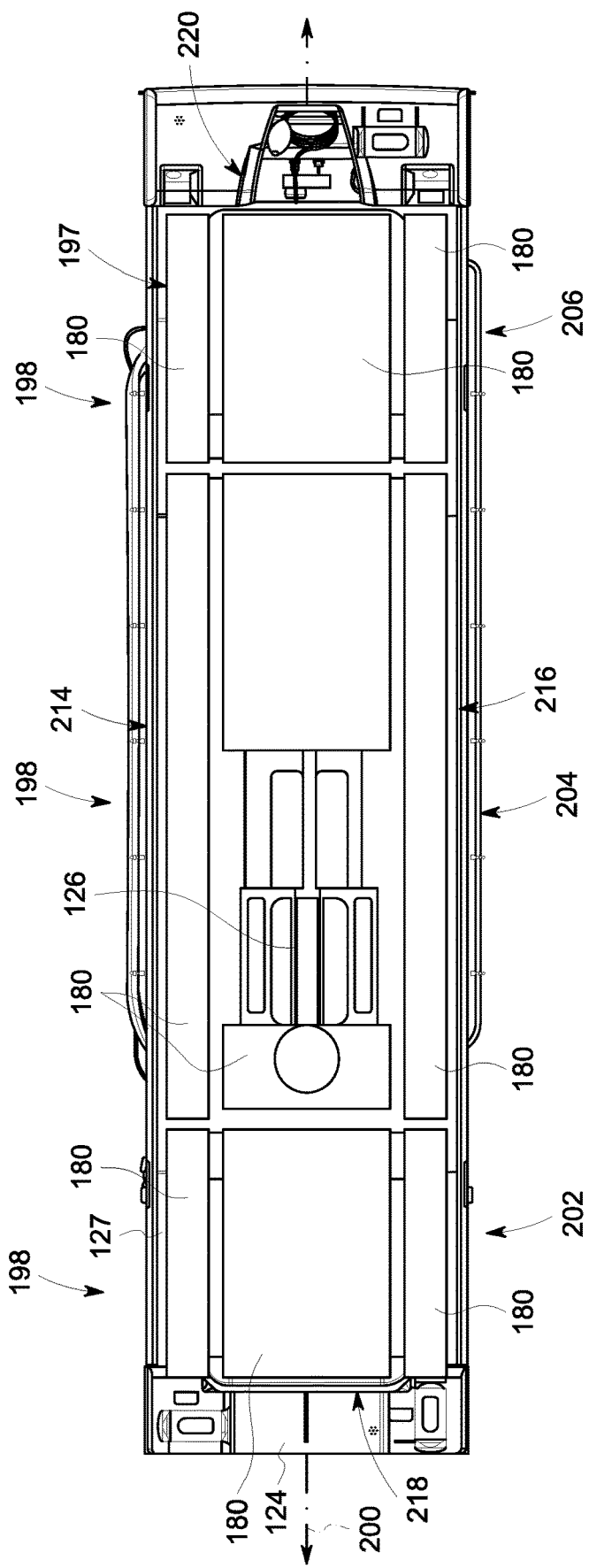
FIG. 10 is a schematic diagram of a top view of a posterior RF receiving coil array assembly being utilized with a pediatric patient, in accordance with aspects of the present disclosure.

FIG. 10 is a schematic diagram of a top view of the posterior RF receiving coil array assembly 196 being utilized with a pediatric patient 126. The posterior RF receiving coil array assembly 196 is similar to that described in FIG. 7. In particular, the posterior RF receiving coil array assembly 196 disposed on the cradle 127 of the table 124 of the MRI system 100 in FIG. 1. As depicted, the posterior RF receiving coil array assembly 196 is disposed across the entirety of the top surface 197 of the cradle 127. The posterior RF receiving coil array assembly 196 is coupled to (e.g., integrated with) the top surface 197 of the cradle 127.

The posterior RF receiving coil array assembly 196 is formed from multiple RF coil array sections 180. As noted above, these sections 180 are padded and each section 180 includes the RF coil having loops. As depicted in FIG. 7, the RF coil array sections 180 located in different regions 198 (e.g., axial locations) along the longitudinal axis 200 of the posterior RF receiving coil array assembly 196 (and the cradle 127). For example, a first plurality of RF coil array sections 180 are located at the first region 202 (e.g., first axial location), a second plurality of RF coil array sections 180 are located at the second region 204 (e.g., second axial location), and a third plurality of RF coil array sections 180 are located at the third region 206 (e.g., third axial location) along the longitudinal axis 200.

Each region 198 is configured to be disposed on the top surface 197 of the cradle 127 below a posterior surface of the pediatric patient 126 to be imaged. As depicted, the pediatric patient 126 is centrally located in the region 204. RF coil array sections 180 flanking the pediatric patient 126 are manipulated (e.g., bent) into a particular position (e.g., bent position) due to having a mechanically resistive structure (e.g., mechanically resistive structure 194 in FIGS. 3 and 4). In particular, these RF coil array sections 180 are bent about the pediatric patient 126 from the posterior surface toward (and disposed about) the anterior surface. Since the RF coil array sections 180 bend about both the posterior and anterior surface of the pediatric patient 126, no additional surface coils (e.g., anterior RF receiving coil array) are needed to image the pediatric patient 126.

Figure 11:
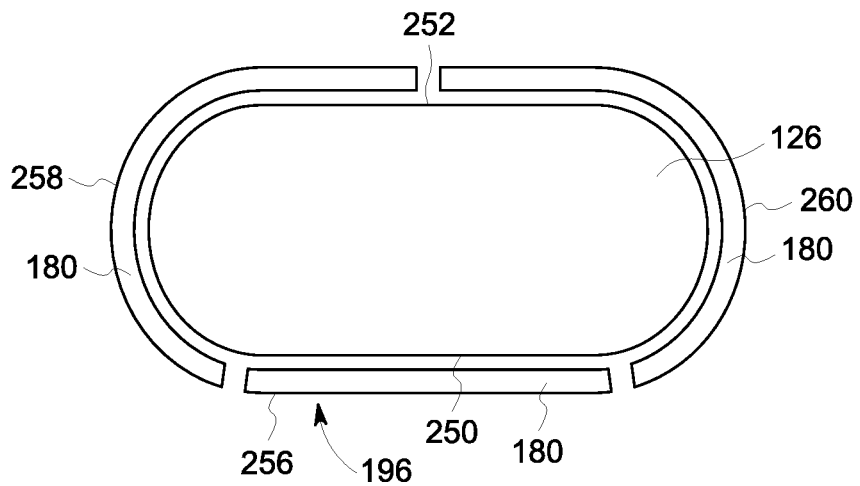
FIG. 11 is a schematic diagram of RF array coil sections of a posterior RF receiving coil array assembly disposed about a portion of a patient, in accordance with aspects of the present disclosure.

FIG. 11 is a schematic diagram of RF array coil sections 180 of the posterior RF receiving coil array assembly 196 disposed about a portion of the patient 126. In FIG. 11, the patient 126 may be a pediatric patient. As depicted, the posterior RF receiving coil array assembly 196 includes multiple RF coil array sections 180. In particular, the posterior RF receiving coil array assembly 196 includes a central RF coil array section 256 flanked by a pair of RF coil array sections 258, 260. Each RF coil array section 256, 258, 260 is a padded section. Each RF coil array section 256, 258, 260 is configured to be disposed beneath the posterior surface 250 of the patient 126 to be imaged. The central RF coil array section 256 is not configured to be manipulated or bent (i.e., the central RF coil array section 256 lacks a mechanically resistive structure). In certain embodiments, the central RF coil array section 256 includes a rigid RF coil. The RF coil array sections 258, 260 each include a mechanically resistive structure that enables each RF coil array section 258, 260 to be manipulated (e.g., bent) into a variety of positions (e.g., bent positions) and maintain these positions without extraneous support (e.g., without support from shims). Each RF coil array section 258, 260 may have a flexible RF coil. As depicted in FIG. 11, each RF coil array sections 258, 260 bent about the patient 126 from the posterior surface 250 toward an anterior surface 252 and then across the anterior surface 252. As depicted in FIG. 11, a separate surface coil array 254 (e.g., anterior RF receiving coil array) is during the MRI imaging of the patient 126. Since the RF coil array sections 258, 260 bend about both the posterior surface 250 and the anterior surface 252 of the pediatric patient 126, no additional surface coils (e.g., anterior RF receiving coil array) are needed to image the pediatric patient 126.

Figure 12:
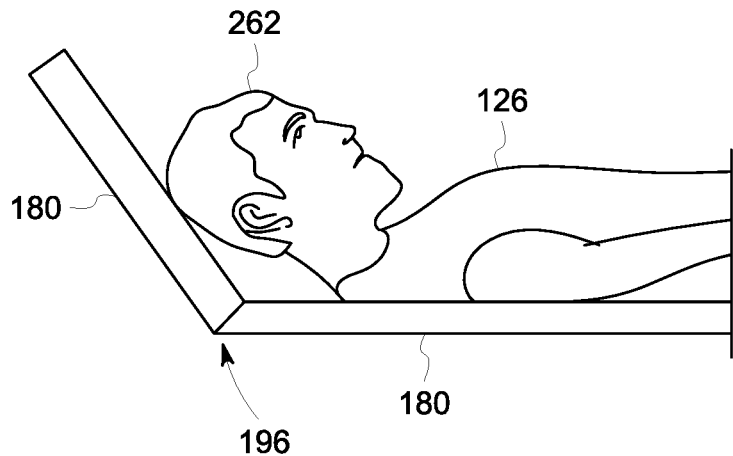
FIG. 12 is a schematic diagram of an RF coil array section of a posterior RF receiving coil array assembly being positioned to lift a portion of a patient (e.g., head), in accordance with aspects of the present disclosure.

FIG. 12 is a schematic diagram of an RF coil array section 180 of the posterior RF receiving coil array assembly 196 being positioned to lift a portion of the patient (e.g., head 262). The patient 126 is disposed across the posterior RF receiving coil array assembly 196 (e.g., as described in FIG. 7). Depending on the orientation of the patient 126 when moved into the bore of the MRI scanner (e.g., head first or feet first), one of the RF coil array sections 180 (e.g., RF coil array section 230 or 232) at the longitudinal ends 218, 220 may be manipulated (e.g., bent) to lift or tilt the head 262 of the patient 126 and maintain the positioning of the head 262 without any extraneous support (e.g., without a shim).

Figure 13:
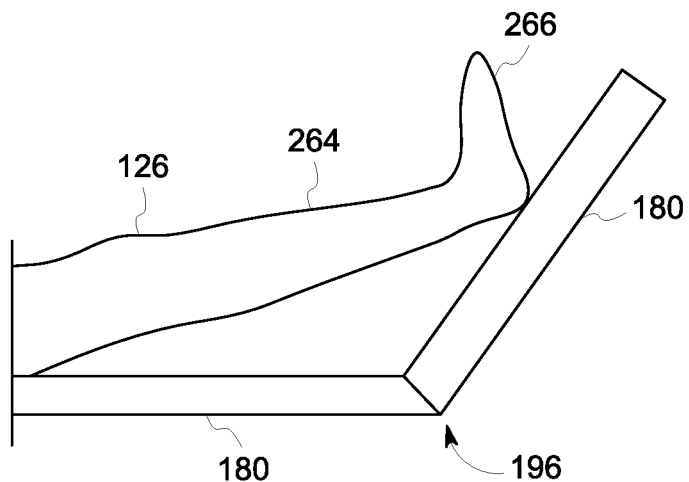
FIG. 13 is a schematic diagram of an RF coil array section of a posterior RF receiving coil array assembly being positioned to lift a portion of a patient (e.g., legs and feet), in accordance with aspects of the present disclosure.

FIG. 13 is a schematic diagram of an RF coil array section 180 of the posterior RF receiving coil array assembly 196 being positioned to lift a portion of the patient (e.g., legs 264 and feet 266). The patient 126 is disposed across the posterior RF receiving coil array assembly 196 (e.g., as described in FIG. 7). Depending on the orientation of the patient 126 when moved into the bore of the MRI scanner (e.g., head first or feet first), one of the RF coil array sections 180 (e.g., RF coil array section 230 or 232) at the longitudinal ends 218, 220 may be manipulated (e.g., bent) to lift or tilt the legs 264 and the feet 266 of the patient 126 and maintain the positioning of the legs 264 and the feet 266 without any extraneous support (e.g., without a shim).

Technical effects of the disclosed subject matter include enabling the posterior RF receiving coil array to be disposed closer to the anatomy of the patient being imaged. The disclosed embodiments enable for better in-table patient positioning and remove the need for comfort tilt accessories. In addition, the disclosed embodiments alleviate issues of carrying around large and somewhat clumsy surface coils for quicker workflow. The disclosed embodiments further provide better contour fitting and comfort to different patient types which boosts image quality. The disclosed embodiments reduce trips to coils closet and overall setup time for the patients while also providing a closer loop-to-anatomy distance to optimize image quality. Even further, by improving workflow with less trips and providing more integrated capability all at the table, the throughput of scanning patients is increased.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A magnetic resonance imaging (MRI) system, comprising:
   an MRI scanner having a bore; and
   a table comprising a cradle and a radio frequency (RF) receiving coil array assembly integrated on a top surface of the cradle, wherein the RF receiving coil array assembly extends across an entirety of the top surface of the cradle, wherein the table is configured to move a subject to be imaged disposed on the RF receiving coil array assembly into and out of the bore of the MRI scanner, wherein the RF receiving coil array assembly comprises a central section comprising a rigid RF coil enclosed within an enclosure, wherein the central section is not configured to be bent, and wherein the RF receiving coil array assembly comprises a plurality of sections that are physically separate from each other and the central section, each section of the plurality of sections comprises a padding and a flexible RF coil comprising a plurality of loops enclosed within a flexible enclosure, and each section of the plurality of sections is configured to be manipulated into a bent position, wherein each section of the plurality of sections is configured to be manipulated into a plurality of different bent positions, wherein the plurality of sections comprises a first section adjacent a first longitudinal end of the central section, a second section adjacent to a second longitudinal end of the central section opposite the first longitudinal end, a third section adjacent to a first side of the central section, a fourth section adjacent to a second side of the central section opposite the first side, the first side and the second side extending between the first longitudinal end and the second longitudinal end, a fifth section and a sixth section flanking the first section, and a seventh section and an eighth section flanking the second section.

2. The MRI system of claim 1, wherein at least one section of the plurality of sections is located adjacent an edge of the cradle.

3. The MRI system of claim 1, wherein at least one section of the plurality of sections is configured to be bent about the subject from a posterior surface of the subject toward an anterior surface of the subject.

4. The MRI system of claim 3, wherein the at least one section of the plurality of sections in the bent position is configured to be disposed about at least a portion of the anterior surface of the subject.

5. The MRI system of claim 1, wherein the RF receiving coil array assembly is configured to be utilized on both a posterior surface and an anterior surface of a pediatric subject without utilizing any additional RF receiving coil array assembly during an imaging scan of the pediatric subject by the MRI system.

6. A radio frequency (RF) receiving coil array assembly for a magnetic resonance imaging (MRI) system, comprising:
 a central section comprising a rigid RF coil enclosed within an enclosure, wherein the central section is not configured to be bent; and
 a plurality of sections that are physically separate from each other and the central section, wherein each section of the plurality of sections comprises a padding and a flexible RF coil comprising a plurality of loops enclosed within a flexible enclosure, and each section of the plurality of sections is configured to be manipulated into a bent position, wherein each section of the plurality of sections is configured to be manipulated into a plurality of different bent positions, wherein the plurality of sections comprises a first section adjacent a first longitudinal end of the central section, a second section adjacent to a second longitudinal end of the central section opposite the first longitudinal end, a third section adjacent to a first side of the central section, a fourth section adjacent to a second side of the central section opposite the first side, the first side and the second side extending between the first longitudinal end and the second longitudinal end, a fifth section and a sixth section flanking the first section, and a seventh section and an eighth section flanking the second section, wherein the RF receiving coil array assembly is configured to be integrated on a top surface of a cradle of a table configured to move a subject to be imaged disposed on the RF receiving coil array assembly into and out of a bore of an MRI scanner of the MRI system, and wherein the RF receiving coil array assembly is configured to extend across an entirety of the top surface of the cradle.

7. The RF receiving coil array assembly of claim 6, wherein at least one section of the plurality of sections is configured to be bent about the subject from a posterior surface of the subject toward an anterior surface of the subject.

8. The RF receiving coil array assembly of claim 6, wherein at least one section of the plurality of sections is located adjacent an edge of the cradle.

* * * * *